(12) United States Patent
Harris et al.

(10) Patent No.: US 10,039,572 B2
(45) Date of Patent: Aug. 7, 2018

(54) POLYAXIAL BONE ANCHOR INCORPORATING A TWO POSITION SADDLE ASSEMBLY

(71) Applicants: Peter M. Harris, Boca Raton, FL (US); James Q. Spitler, Boca Raton, FL (US)

(72) Inventors: Peter M. Harris, Boca Raton, FL (US); James Q. Spitler, Boca Raton, FL (US)

(73) Assignee: FloSpine LLC, Boca Raton, FL (US)

( * ) Notice: Subject to any disclaimer, the term of this patent is extended or adjusted under 35 U.S.C. 154(b) by 315 days.

(21) Appl. No.: 14/618,233

(22) Filed: Feb. 10, 2015

(65) Prior Publication Data
US 2015/0230829 A1 Aug. 20, 2015

Related U.S. Application Data

(60) Provisional application No. 61/940,687, filed on Feb. 17, 2014.

(51) Int. Cl.
*A61B 17/70* (2006.01)

(52) U.S. Cl.
CPC ...... *A61B 17/7037* (2013.01); *A61B 17/7082* (2013.01)

(58) Field of Classification Search
CPC ........ A61B 17/7001; A61B 17/7032–17/7046; A61B 17/8605–17/866
See application file for complete search history.

(56) References Cited

U.S. PATENT DOCUMENTS

| | | | |
|---|---|---|---|
| 5,672,176 A | 9/1997 | Biedermann et al. | |
| 8,197,517 B1* | 6/2012 | Lab | A61B 17/7037 606/268 |
| 8,574,274 B2* | 11/2013 | Courtney | A61B 17/7037 606/266 |
| 9,345,519 B1* | 5/2016 | Poirier | A61B 17/7032 |
| 2010/0198272 A1* | 8/2010 | Keyer | A61B 17/7082 606/302 |
| 2010/0234902 A1* | 9/2010 | Biedermann | A61B 17/7032 606/305 |
| 2011/0152949 A1* | 6/2011 | Biedermann | A61B 17/7037 606/305 |
| 2012/0330364 A1* | 12/2012 | Jacofsky | A61B 17/7032 606/278 |
| 2015/0282844 A1* | 10/2015 | Vedula | A61B 17/7032 606/305 |
| 2016/0361096 A1* | 12/2016 | van der Pol | A61B 17/7076 |
| 2017/0189075 A1* | 7/2017 | Vedula | A61B 17/7032 |

\* cited by examiner

*Primary Examiner* — Jacqueline Johanas
*Assistant Examiner* — Tessa Matthews
(74) *Attorney, Agent, or Firm* — Clements Bernard Walker PLLC; Christopher L. Bernard

(57) ABSTRACT

A polyaxial bone anchor assembly, comprising: a threaded screw portion comprising a head end; a head body disposed concentrically about the head end of the threaded screw portion; and a saddle assembly disposed within the head body and selectively engaging the head end of the threaded screw portion; wherein, when the saddle assembly is translated within the head body into a first locked position, the head body is coupled to the threaded screw portion such that disengagement of the head body from the threaded screw portion is allowed; and wherein, when the saddle assembly is translated within the head body into a second locked position, the head body is coupled to the threaded screw portion such that disengagement of the head body from the threaded screw portion is prevented.

13 Claims, 12 Drawing Sheets

POLYAXIAL BONE ANCHOR INCORPORATING A TWO POSITION SADDLE ASSEMBLY

CROSS-REFERENCE TO RELATED APPLICATION

The present patent application/patent claims the benefit of priority of U.S. Provisional Patent Application No. 61/940,687, filed on Feb. 17, 2014, and entitled "TWO POSITION SADDLE FOR USE IN MOUNTABLE POLYAXIAL BONE ANCHOR," the contents of which are incorporated in full by reference herein.

FIELD OF THE INVENTION

The present invention relates generally to a polyaxial bone anchor, or pedicle screw, for the stabilization and fixation of bones, such as vertebrae of the spine. More specifically, the present invention relates to a polyaxial bone anchor, or pedicle screw, that incorporates a two position saddle assembly, such that the polyaxial bone anchor, or pedicle screw, can be placed in either a pre-assembled configuration or a disassembled configuration.

BACKGROUND OF THE INVENTION

A variety of conventional pedicle screws are known to those of ordinary skill in the art. These pedicle screws typically consist of a threaded screw portion including an enlarged head end and a head body. The threaded screw portion engages a pedicle of a vertebra of the spine, and the head body engages the threaded screw portion, optionally by passing the threaded screw portion through a hole manufactured into the bottom of the head body until the head end is seated in the bottom portion of the head body. The pedicle screws can be monoaxial or polyaxial, allowing the head body multiple degrees of freedom with respect to the threaded screw portion. Once placed, rods are inserted into the head bodies of adjacent pedicle screws and set screws are placed to simultaneously secure the head bodies to their respective threaded screw portions and to lock the rods in place. A rigid framework is thereby formed, stabilizing and fixing the vertebrae of the spine.

Typically, these pedicle screws are placed in a pre-assembled configuration, with the head body joined to the threaded screw portion. It is desirable, however, that a surgeon have a pedicle screw that may be placed in a disassembled configuration, first placing the threaded screw portion, and then "snapping" the head body onto the threaded screw portion, at all times maintaining the polyaxial nature of the pedicle screw such that rods may be inserted as necessary before everything is locked together. The present invention provides such a pedicle screw.

BRIEF SUMMARY OF THE INVENTION

In various exemplary embodiments, the present invention provides a bone anchor, or pedicle screw, that includes a threaded screw portion, a head body, and a saddle assembly. A rod is dropped into the head body on top of the saddle assembly and locked into place using a set screw. The head body can accommodate rod sizes between about 5.5 and 6 mm in diameter, for example. The bone anchor is polyaxial, such that the head body can rotate in a conical circle with respect to the threaded screw portion before it is locked into place by the rod and the set screw. The bone anchor can be pre-assembled in one piece before it is placed in a patient. Alternatively, the threaded screw portion can be placed in the patient minus the head body and the saddle assembly. Once all of the threaded screw portions are placed, the saddle assemblies can be pre-assembled into the head bodies, and then the head bodies can be "snapped" onto the threaded screw portions, still maintaining their polyaxial nature.

In this latter methodology, the saddle assembly has two locking positions within the head body. During manufacture, for example, the saddle assembly is pressed into the head body, where it "snaps" into a first recessed groove. This is the first locking position for the saddle assembly. The head body is then placed on an insertion instrument that grips the outside of the head body and has a flat boss that engages the interior of the head body, such that the saddle assembly is prevented from backing out of the head body. The head body and saddle assembly are then "snapped" onto the head end of the threaded screw portion that is already anchored in bone. The mechanics of this engagement are described in greater detail herein below, as are all the components of the bone anchor. At this point, the head body still has sufficient rotation to allow the surgeon to place and manipulate the rods in the head bodies. The set screws are then placed. The tightening of the set screw then, through the rod, forces the saddle assembly down, where it "snaps" into a second recessed groove and a second locking position within the head body. In this second locking position, the saddle assembly secures the head body rigidly to the head end of the treaded screw portion, and the set screw secures the rod. This completes the assembly of the rigid construct.

Optionally, the screw thread form is between a cortical thread and a cancellous thread to provide maximum pullout strength. The set screw has a reverse square thread, for example, to prevent head splay after final tightening. The head body has cutouts on the sides to allow for the attachment of rod reducers, minimally invasive (MIS) instrumentation, and the like. Optionally, these cutouts have a 15 degree undercut to better grip the reduction and MIS instruments. Finally, the saddle assembly incorporates "wings" to prevent it from rotating within the head body. Again, all components of the bone anchor are described in greater detail herein below. It should be noted that all components of the bone anchor can be made of any suitable surgically implantable material, well known to those of ordinary skill in the art.

In one exemplary embodiment, the present invention provides a polyaxial bone anchor assembly, comprising: a threaded screw portion comprising a head end; a head body disposed concentrically about the head end of the threaded screw portion; and a saddle assembly disposed within the head body and engaging the head end of the threaded screw portion; wherein, when the saddle assembly is translated within the head body into a locked position, the head body is coupled to the threaded screw portion such that disengagement of the head body from the threaded screw portion is prevented. The saddle assembly is translated within the head body via a rod disposed adjacent to the saddle assembly, wherein the rod is disposed partially within the head body through at least one recess manufactured into a side of the head body. The rod engages a recess manufactured into an upper surface of the saddle assembly. The saddle assembly is translated within the head body via a set screw disposed adjacent to the rod opposite the saddle assembly, wherein the set screw comprises external threads that engage internal threads manufactured into an interior portion of the head body. The saddle assembly comprises a plurality of concentrically arranged deflectable petal structures disposed about a lower portion of the saddle assembly that engage the head end of the threaded screw portion. The head end of the threaded screw portion is disposed through a hole manufactured in a lower portion of the head body.

In another exemplary embodiment, the present invention provides a polyaxial bone anchor assembly, comprising: a threaded screw portion comprising a head end; a head body disposed concentrically about the head end of the threaded screw portion; and a saddle assembly disposed within the head body and selectively engaging the head end of the threaded screw portion; wherein, when the saddle assembly is translated within the head body into a first locked position, the head body is coupled to the threaded screw portion such that disengagement of the head body from the threaded screw portion is allowed; and wherein, when the saddle assembly is translated within the head body into a second locked position, the head body is coupled to the threaded screw portion such that disengagement of the head body from the threaded screw portion is prevented. The saddle assembly is press fit into the first locked position within the head body prior to the saddle assembly engaging the head end of the threaded screw portion. The saddle assembly is translated into the second locked position within the head body via a rod disposed adjacent to the saddle assembly, wherein the rod is disposed partially within the head body through at least one recess manufactured into a side of the head body. The rod engages a recess manufactured into an upper surface of the saddle assembly. The saddle assembly is translated into the second locked position within the head body via a set screw disposed adjacent to the rod opposite the saddle assembly, wherein the set screw comprises external threads that engage internal threads manufactured into an interior portion of the head body. The saddle assembly comprises a plurality of concentrically arranged deflectable petal structures disposed about a lower portion of the saddle assembly that selectively engage the head end of the threaded screw portion. The head end of the threaded screw portion is disposed through a hole manufactured in a lower portion of the head body subsequent to the placement of the threaded screw portion in bone.

In a further exemplary embodiment, the present invention provides a polyaxial bone anchor method, comprising: providing a threaded screw portion comprising a head end; providing a head body disposed concentrically about the head end of the threaded screw portion; providing a saddle assembly disposed within the head body and selectively engaging the head end of the threaded screw portion; translating the saddle assembly within the head body into a first locked position, wherein, when the saddle assembly is translated within the head body into the first locked position, the head body is coupled to the threaded screw portion such that disengagement of the head body from the threaded screw portion is allowed; and translating the saddle assembly within the head body into a second locked position, wherein, when the saddle assembly is translated within the head body into the second locked position, the head body is coupled to the threaded screw portion such that disengagement of the head body from the threaded screw portion is prevented. The saddle assembly is press fit into the first locked position within the head body prior to the saddle assembly engaging the head end of the threaded screw portion. The saddle assembly is translated into the second locked position within the head body via a rod disposed adjacent to the saddle assembly, wherein the rod is disposed partially within the head body through at least one recess manufactured into a side of the head body. The rod engages a recess manufactured into an upper surface of the saddle assembly. The saddle assembly is translated into the second locked position within the head body via a set screw disposed adjacent to the rod opposite the saddle assembly, wherein the set screw comprises external threads that engage internal threads manufactured into an interior portion of the head body. The saddle assembly comprises a plurality of concentrically arranged deflectable petal structures disposed about a lower portion of the saddle assembly that selectively engage the head end of the threaded screw portion. The head end of the threaded screw portion is disposed through a hole manufactured in a lower portion of the head body subsequent to the placement of the threaded screw portion in bone.

In a still further exemplary embodiment, the present invention provides a polyaxial bone anchor retention and placement instrument, comprising: an elongate shaft portion comprising a proximal end and a distal end; a head body retention assembly coupled to the proximal end of the elongate shaft portion, wherein the head body retention assembly comprises a pair of opposed elongate structures configured to selectively engage a corresponding pair of opposed recesses manufactured into an exterior or interior portion of a head body of a polyaxial bone anchor, and wherein the head body retention assembly further comprises a central boss or shaft structure that selectively protrudes into an interior portion of the head body and contacts a saddle assembly disposed therein such that the saddle assembly is not allowed to back out of the head body; and a handle portion coupled to the distal end of the elongate shaft portion. Each of the pair of opposed elongate structures comprises an internal or external protrusion that is configured to selectively engage the corresponding recess manufactured into the exterior or interior portion of the head body. The head body retention assembly is coupled to the head body and contacts the saddle assembly while the head body and saddle assembly are coupled to a head end of a threaded screw portion of the polyaxial bone anchor.

BRIEF DESCRIPTION OF THE DRAWINGS

The present invention is illustrated and described herein with reference to the various drawings, in which like reference numbers are used to refer to like assembly components, and in which.

DETAILED DESCRIPTION OF THE INVENTION

Figure 1:
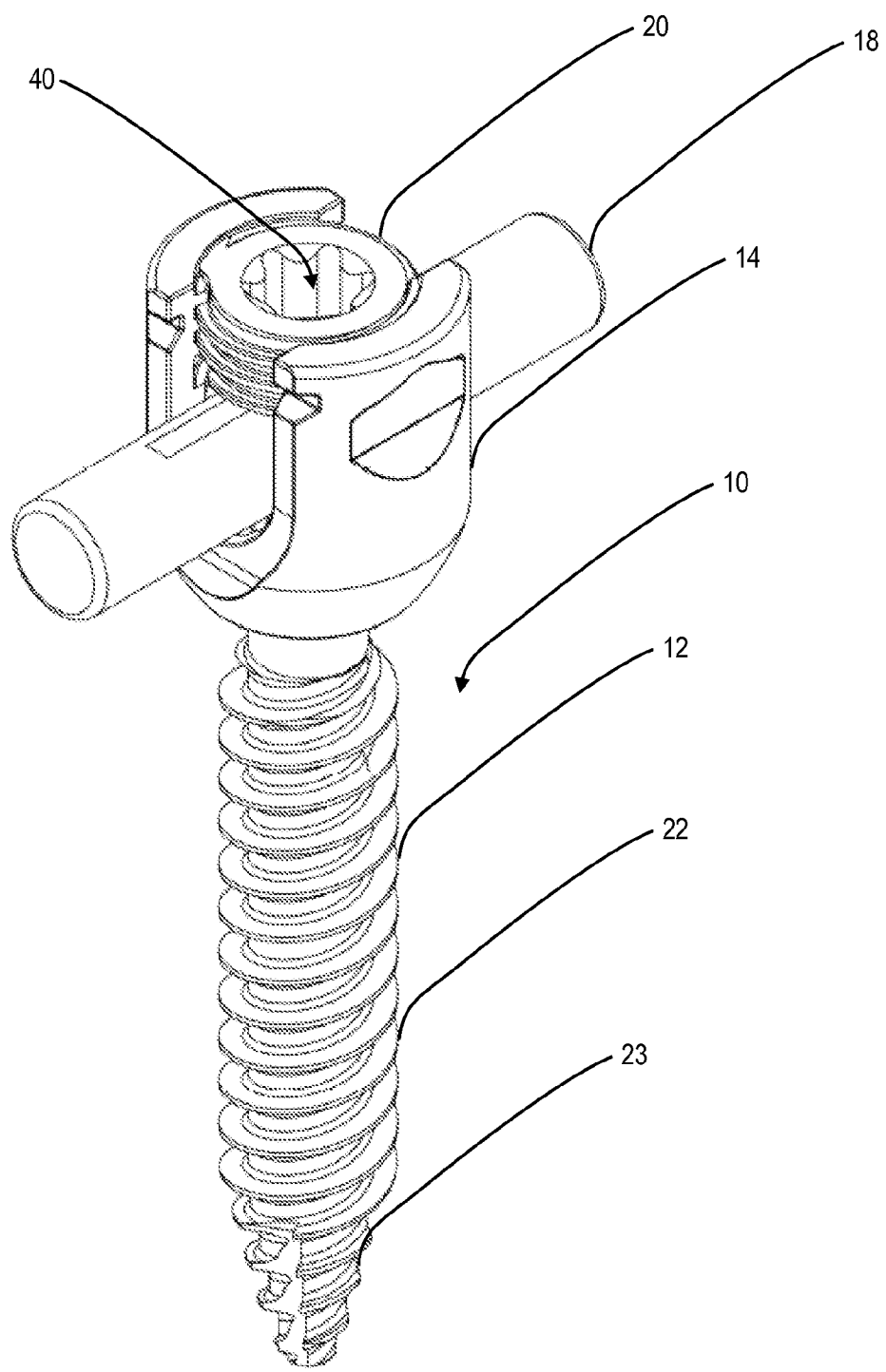
FIG. 1 is a perspective view of one exemplary embodiment of the bone anchor of the present invention in an assembled configuration, including the placement and retention of a rod and a set screw.
Figure 2:
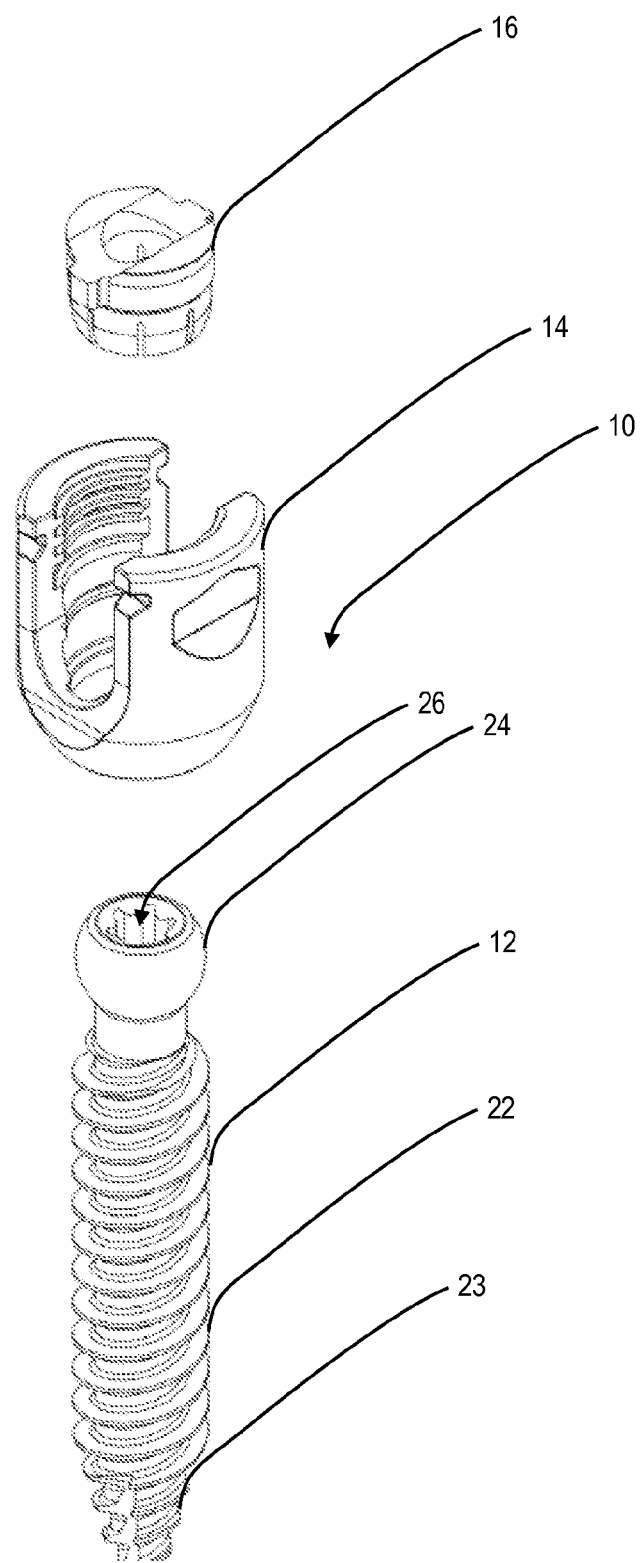
FIG. 2 is a perspective view of one exemplary embodiment of the bone anchor of the present invention in a disassembled configuration.

Referring now specifically to FIGS. 1 and 2, in one exemplary embodiment, the present invention provides a bone anchor 10, or pedicle screw, that includes a threaded screw portion 12, a head body 14, and a saddle assembly 16 (FIG. 2). When assembled, a rod 18 (FIG. 1) is dropped into the head body 14 on top of the saddle assembly 16 and locked into place using a set screw 20 (FIG. 1). The head body 14 can accommodate rod sizes between about 5.5 and 6 mm in diameter, for example. Optionally, the screw thread form is between a cortical thread and a cancellous thread to provide maximum pullout strength. The set screw 20 has a reverse square thread, for example, to prevent head splay after final tightening. The bone anchor 10 is polyaxial, such that the head body 14 can rotate in a conical circle with respect to the threaded screw portion 12 before it is locked into place by the rod 18 and the set screw 20. As described herein above and in greater detail herein below, the bone anchor 10 can be pre-assembled in one piece before it is placed in a patient. Alternatively, the threaded screw portion 12 can be placed in the patient minus the head body 14 and the saddle assembly 16. Once all of the threaded screw portions 12 are placed, the saddle assemblies 16 can be pre-assembled into the head bodies 14, and then the head bodies 14 can be "snapped" onto the threaded screw portions 12, still maintaining their polyaxial nature. Again, it should be noted that all components of the bone anchor 10 can be made of any suitable surgically implantable material, well known to those of ordinary skill in the art.

The threaded screw portion 12 includes a threaded shaft portion 22 and a threaded tapered end portion 23 that collectively engage and affix the threaded screw portion 12 to the target bone, as with conventional pedicle screws. The threaded screw portion 12 also includes a head end 24 (FIG. 2) including a recessed driver receptacle 26 (FIG. 2) that is configured to receive a driver instrument for driving the threaded screw portion 12 into the target bone. Again, this is similar to conventional pedicle screws.

Figure 3:
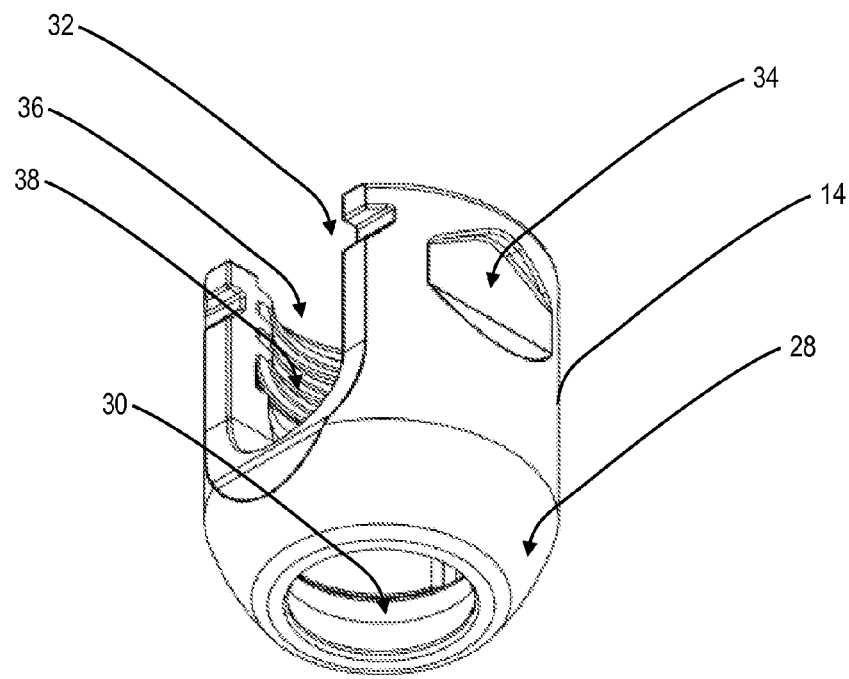
FIG. 3 is a perspective view of one exemplary embodiment of the head body of the bone anchor of the present invention.

Referring now specifically to FIG. 3, in one exemplary embodiment, the head body 14 has a generally cylindrical shape with a partially closed and, optionally, tapered bottom portion 28. This bottom portion 28 defines a hole 30 through which the head end 26 (FIG. 2) of the threaded screw portion 12 (FIGS. 1 and 2) passes. The bottom portion 28 includes any number and/or configuration of cutouts 32, 34 for receiving retention and placement instrumentation, reduction and MIS instruments, etc. Specifically, in this exemplary embodiment, the bottom portion 28 includes cutouts 34 for receiving an insertion instrument, described herein above and in greater detail herein below, that grips the outside of the head body 14 and has a flat boss that engages the interior of the head body 14, such that the saddle assembly 16 (FIG. 2) is prevented from backing out of the head body 14 when inserted. Optionally, these cutouts 32, 34 have a 15 degree undercut to better grip the retention, placement, reduction, and MIS instruments. The head body 14 further includes a pair of opposed recesses 36 that are configured to receive the rod 18 (FIG. 1) into/through the head body 14. Finally, the head body 14 includes internal threading 38 that is configured to receive and retain the externally threaded set screw 20 (FIG. 1), which of course includes a recessed driver receptacle 40 (FIG. 1) that is configured to receive a driver instrument for screwing the set screw 20 into the head body 14. Again, this is similar to conventional pedicle screws.

Figure 4:
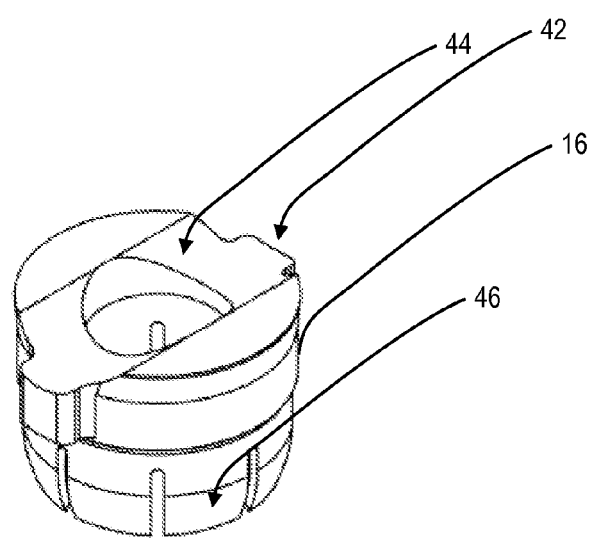
FIG. 4 is a perspective view of one exemplary embodiment of the saddle assembly of the bone anchor of the present invention.

Referring now specifically to FIG. 4, in one exemplary embodiment, the saddle assembly 16 has a generally cylindrical shape and, when assembled, sits inside of the head body 14 (FIGS. 1-3). A plurality of wing like protrusions 42 extend concentrically outward from the sides of the saddle assembly 16 and engage the rod recesses 36 (FIG. 3) of the head body 14, such that rotation of the saddle assembly 16 within the head body 14 is prevented. In general, the saddle assembly 16 is allowed to travel up and down within the head body 14, such that the position of the saddle assembly within the head body 14 can be adjusted. The saddle assembly 16 also includes a recess 44 that is configured to receive and orient the rod 18 (FIG. 1) when placed. The saddle assembly 16 further includes a plurality of deflectable petal structures 46 disposed concentrically around the bottom portion thereof, and configured to "snap" onto the head end 24 (FIG. 2) of the threaded screw portion 12 (FIGS. 1 and 2) when the head end 24 of the threaded screw portion 12 is disposed through and into the head body 14, thereby securing the threaded screw portion 12, the head body 14, and the saddle assembly 16 together, as is described in greater detail herein below.

Figure 5:
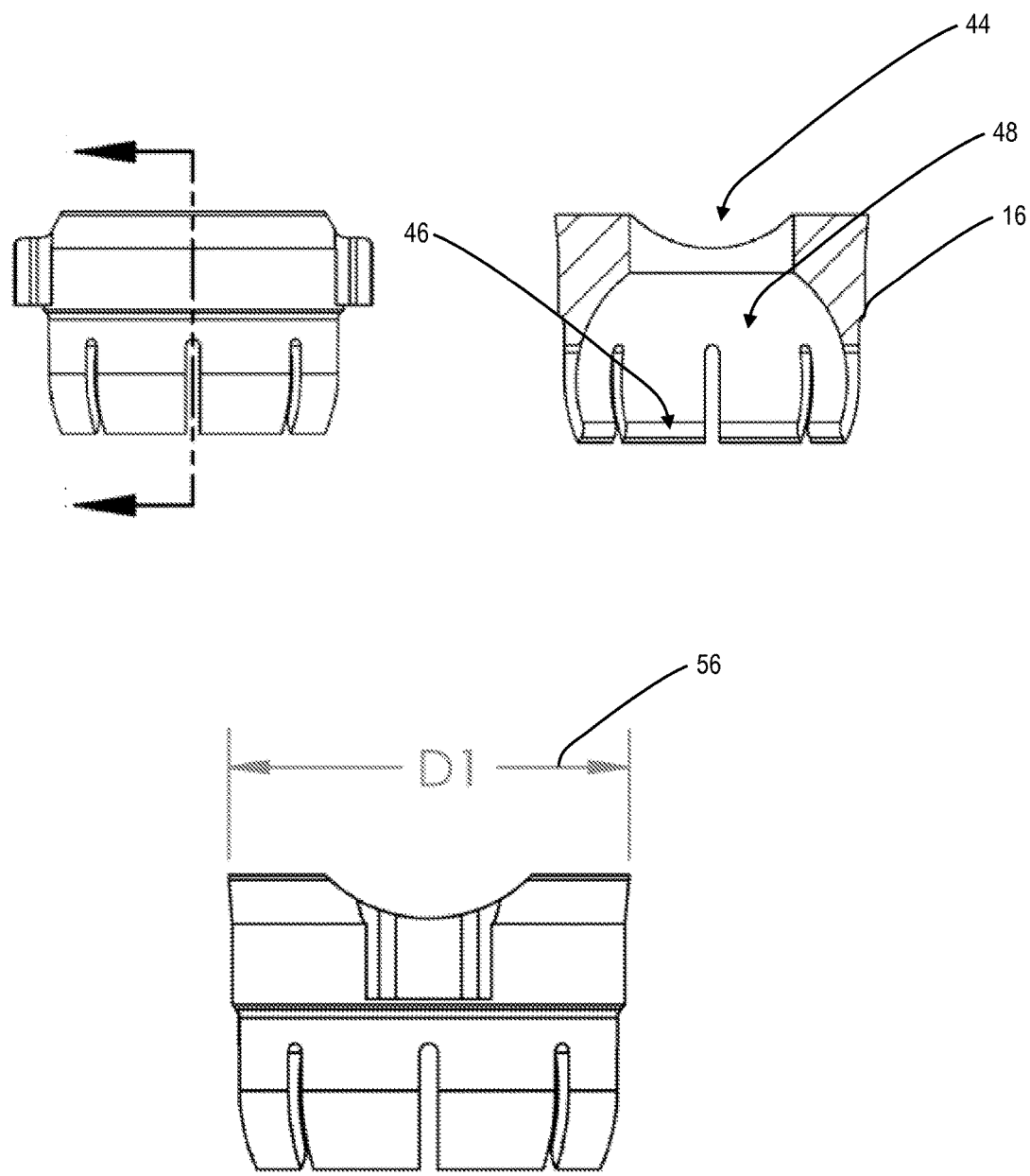
FIG. 5 is a cross-sectional side view of one exemplary embodiment of the saddle assembly of the bone anchor of the present invention.

Referring now specifically to FIG. 5, in one exemplary embodiment, the interior volume 48 of the saddle assembly 16 is sized and shaped such that it substantially conforms to the size and shape of the head end 24 (FIG. 2) of the threaded screw portion 12 (FIGS. 1 and 2). In this exemplary embodiment, the head end 24 of the threaded screw portion 12 has a substantially circular or elliptical shape, although it will be readily apparent to those of ordinary skill in the art that other suitable shapes can be utilized. In this manner, when the petal structures 46 are deflected by the head end 24 of the threaded screw portion 12 and the saddle assembly 16 is "snapped" onto the head end 24 of the threaded screw portion 12, the saddle assembly 16 snugly engages the head end 24 of the threaded screw portion 12. In general, the outside surface of the saddle 16 is spherical/conical and mates with the spherical/conical inside surface of the head body 14, which locks them together.

Figure 6:
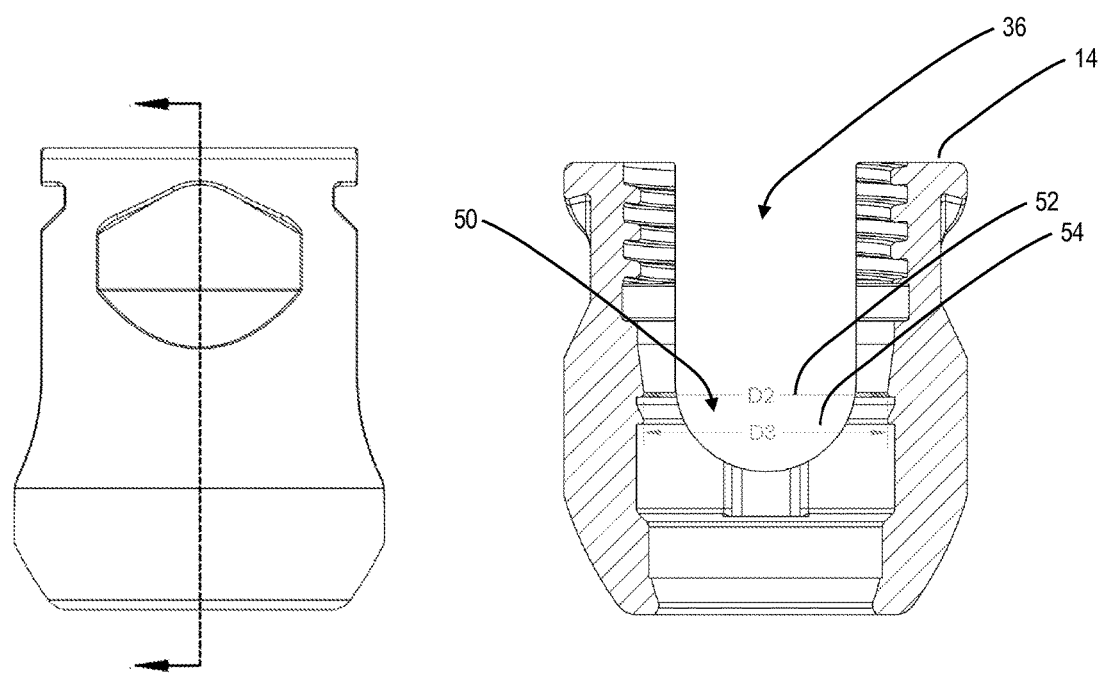
FIG. 6 is a cross-sectional side view of one exemplary embodiment of the head body of the bone anchor of the present invention.
Figure 7:
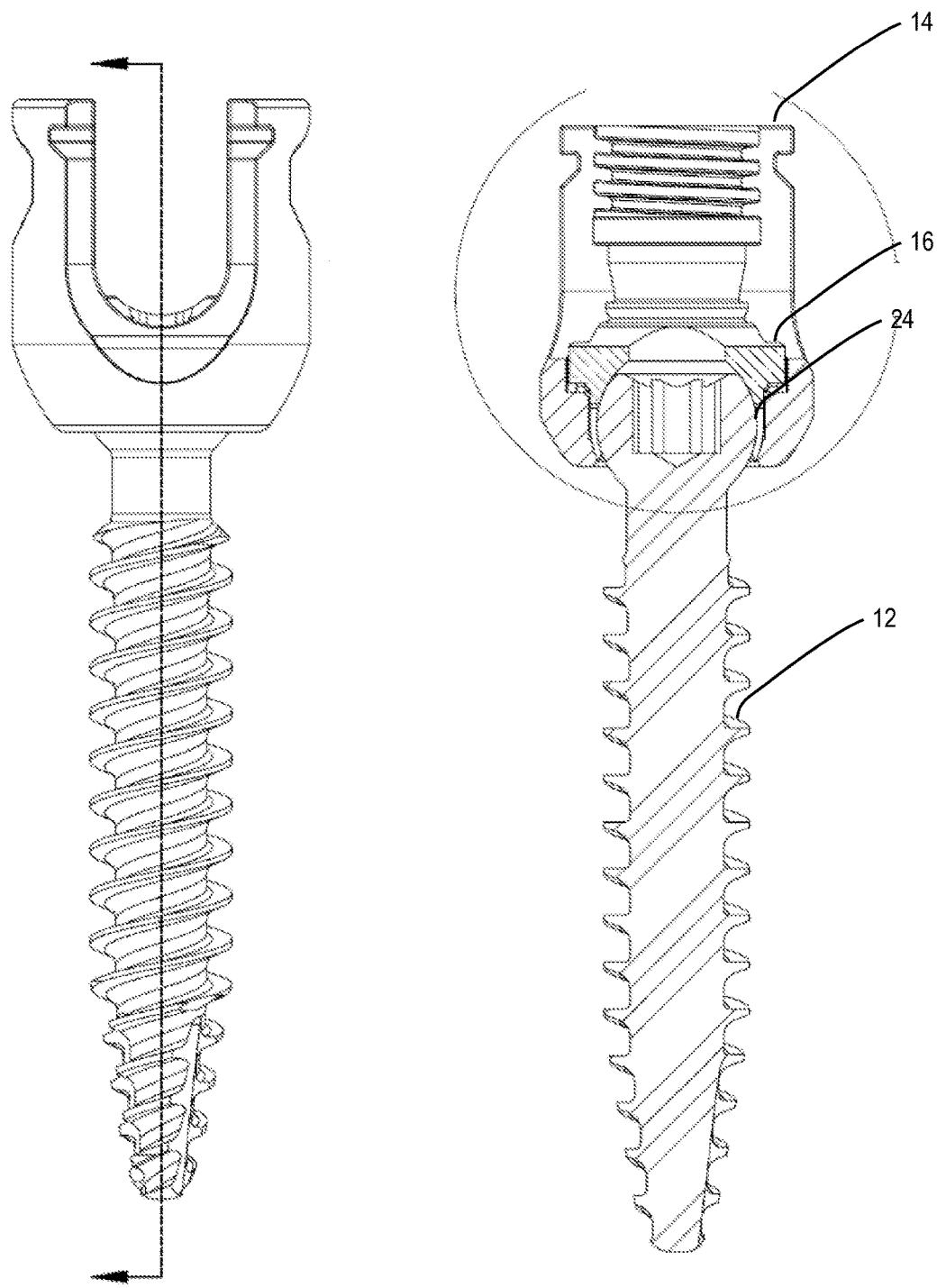
FIG. 7 is a cross-sectional side view of one exemplary embodiment of the bone anchor of the present invention in an assembled configuration, minus the placement and retention of the rod and the set screw.

Referring now specifically to FIG. 6, in one exemplary embodiment, the interior volume 50 of the head body 14 utilizes a plurality of different internal diameters that, along with a plurality of recesses, form a plurality of detents or retention points for the saddle assembly 16 (FIGS. 2-5) as it is progressively inserted deeper into the head body 14. The saddle assembly 16 has two locking positions within the head body 14. During manufacture, for example, the saddle assembly 16 is pressed into the head body 14, where it "snaps" into a first recessed groove 52—diameter D2. This is the first locking position for the saddle assembly 16. The head body 14 is then placed on an insertion instrument that grips the outside of the head body 14 and has a flat boss that engages the interior of the head body 14, such that the saddle assembly 16 is prevented from backing out of the head body. The head body 14 and saddle assembly 16 are then "snapped" onto the head end 24 (FIG. 2) of the threaded screw portion (FIGS. 1 and 2) that is already anchored in bone. At this point, the head body 14 still has sufficient rotation to allow the surgeon to place and manipulate the rods 18 (FIG. 1) in the head bodies 14. The set screws 20 (FIG. 1) are then placed. The tightening of the set screw 20 then, through the rod 18, forces the saddle assembly 16 down, where it "snaps" into a second recessed groove 54—diameter D3—and a second locking position within the head body 14. The saddle assembly 16 has a major diameter 56—diameter D1—that is slightly larger than diameters D2 or D3, such that the saddle assembly 16 is press fit into the head body 14, and "snaps" into the various recesses manufactured therein. In this second locking position, the saddle assembly 16 secures the head body 14 rigidly to the head end 24 of the treaded screw portion 12, and the set screw 20 secures the rod 18. This completes the assembly of the rigid construct, with the head end 24 of the threaded screw portion 12 snugly engaging the saddle assembly 16, and the saddle assembly 16 being secured in the second locking position within the head body 14. This assembled configuration is further illustrated in FIG. 7.

Figure 8:
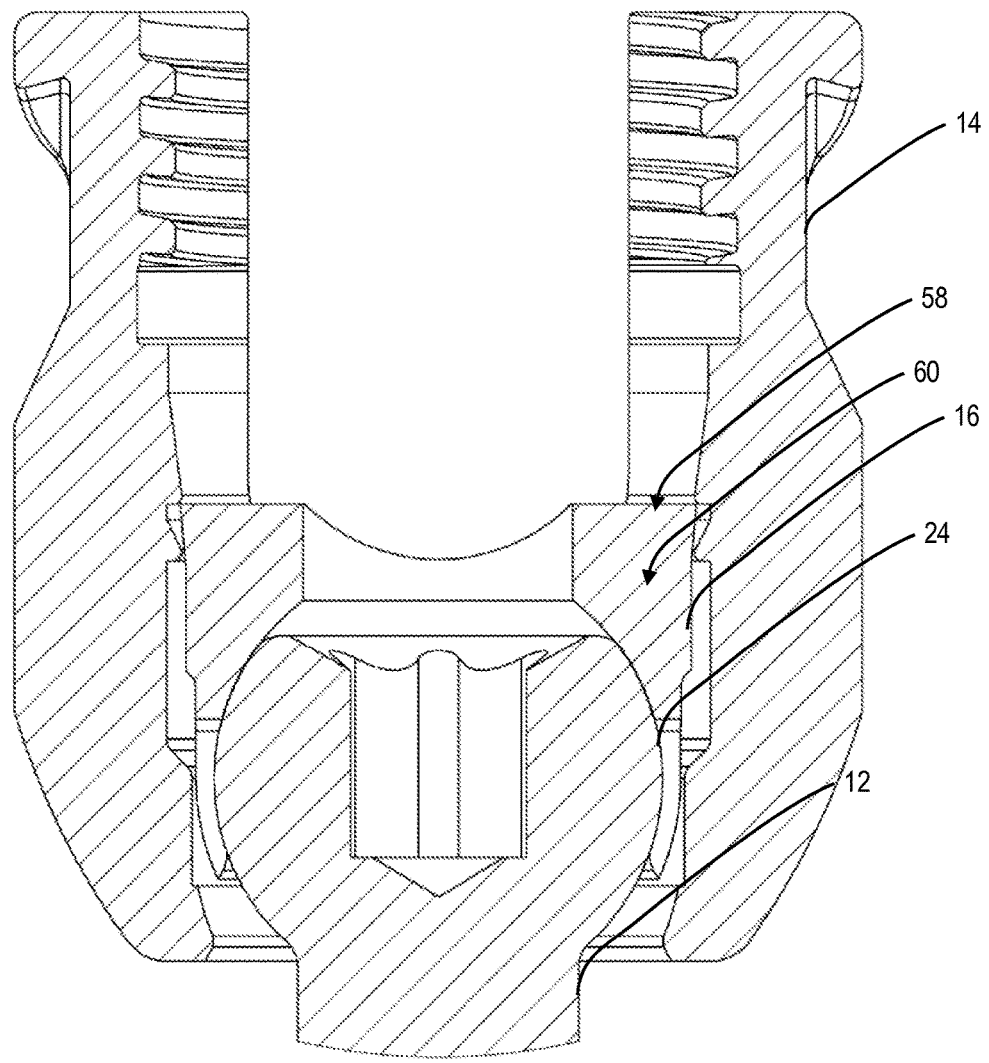
FIG. 8 is a partial cross-sectional side view of one exemplary embodiment of the bone anchor of the present invention in an assembled configuration, minus the placement and retention of the rod and the set screw.

Referring now specifically to FIG. 8, in one exemplary embodiment, the saddle assembly 16 is disposed in the first locking position 58, with the head end 24 of the threaded screw portion 12 "snapped" into the saddle assembly 16. In this configuration, the head body 14 is still free to move with respect to the threaded screw portion 12.

Figure 9:
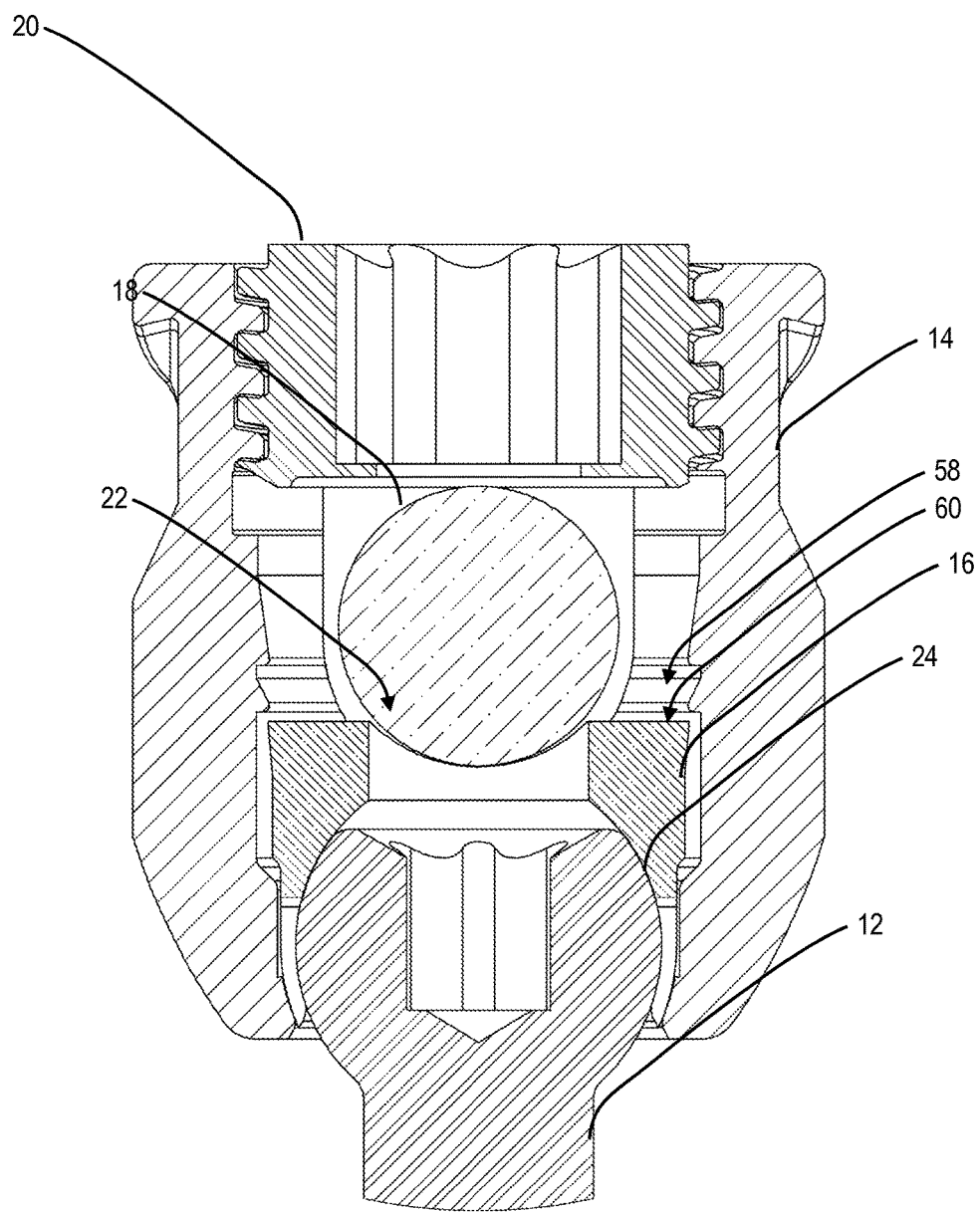
FIG. 9 is a partial cross-sectional side view of one exemplary embodiment of the bone anchor of the present invention in an assembled configuration, including the placement and retention of the rod and the set screw.

Referring now specifically to FIG. 9, in one exemplary embodiment, the saddle assembly 16 is driven into the second locking position 60 via tightening of the set screw 20 and the deflection of the rod 18 deeper into the head body 14, with the head end 24 of the threaded screw portion 12 still "snapped" into the saddle assembly 16. It should be noted that the rod 18 sits in the corresponding recess 44 of the saddle assembly 16. In this configuration, the head body 14 is secured with respect to the threaded screw portion 12. The rod 18 is also locked firmly into place.

Figure 10:
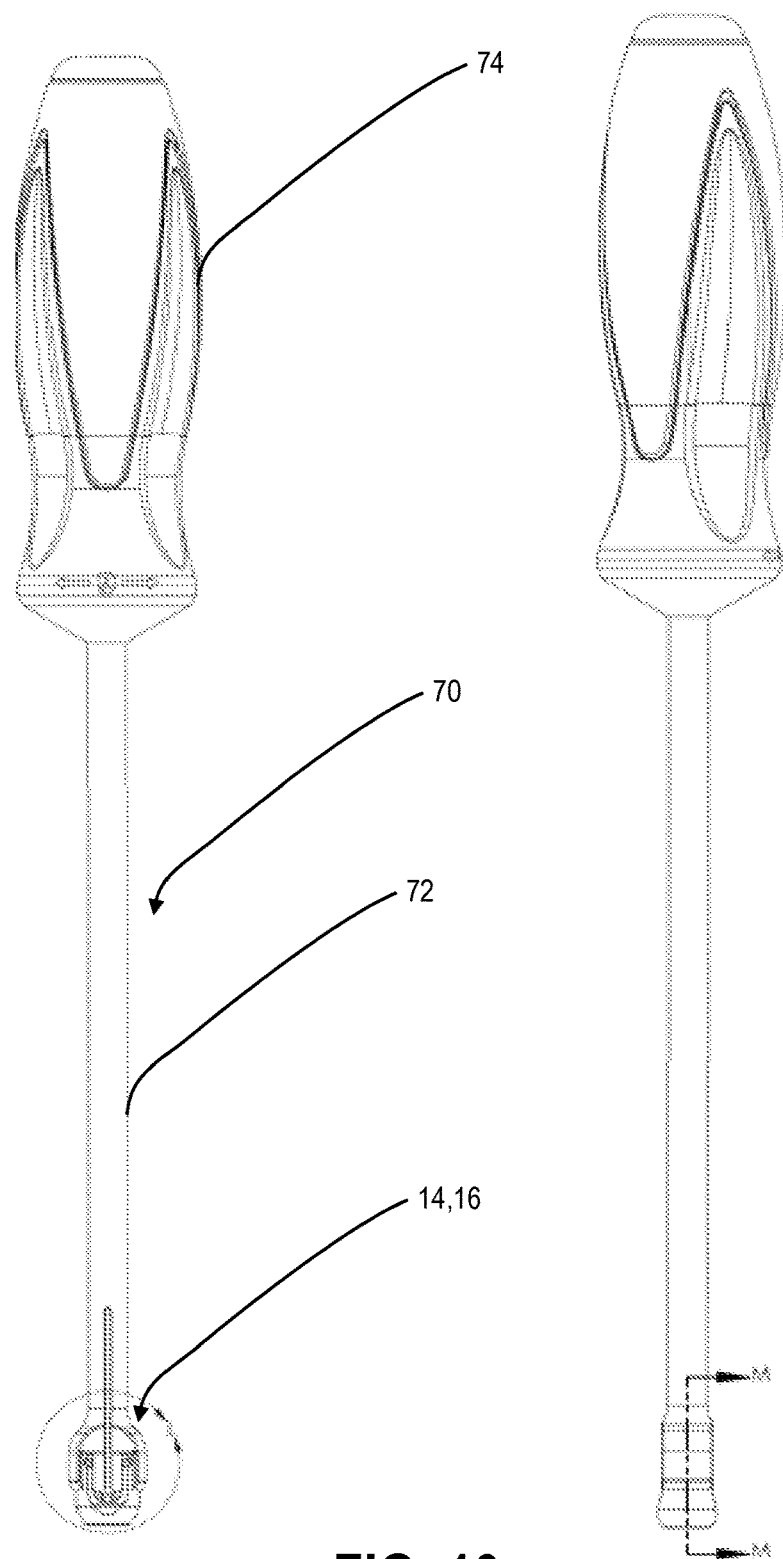
FIG. 10 is a side view of one exemplary embodiment of the head body retention and placement instrument of the present invention, with an engaged head body and saddle assembly.

Referring now specifically to FIG. 10, in one exemplary embodiment, the head body retention and placement instrument 70—includes an elongate shaft portion 72. The head body 14 and saddle assembly 16 are selectively coupled to a proximal end of the elongate shaft portion 72. A distal end of the elongate shaft portion 72 includes a handle portion 74, by which the instrument is manipulated.

Figure 11:
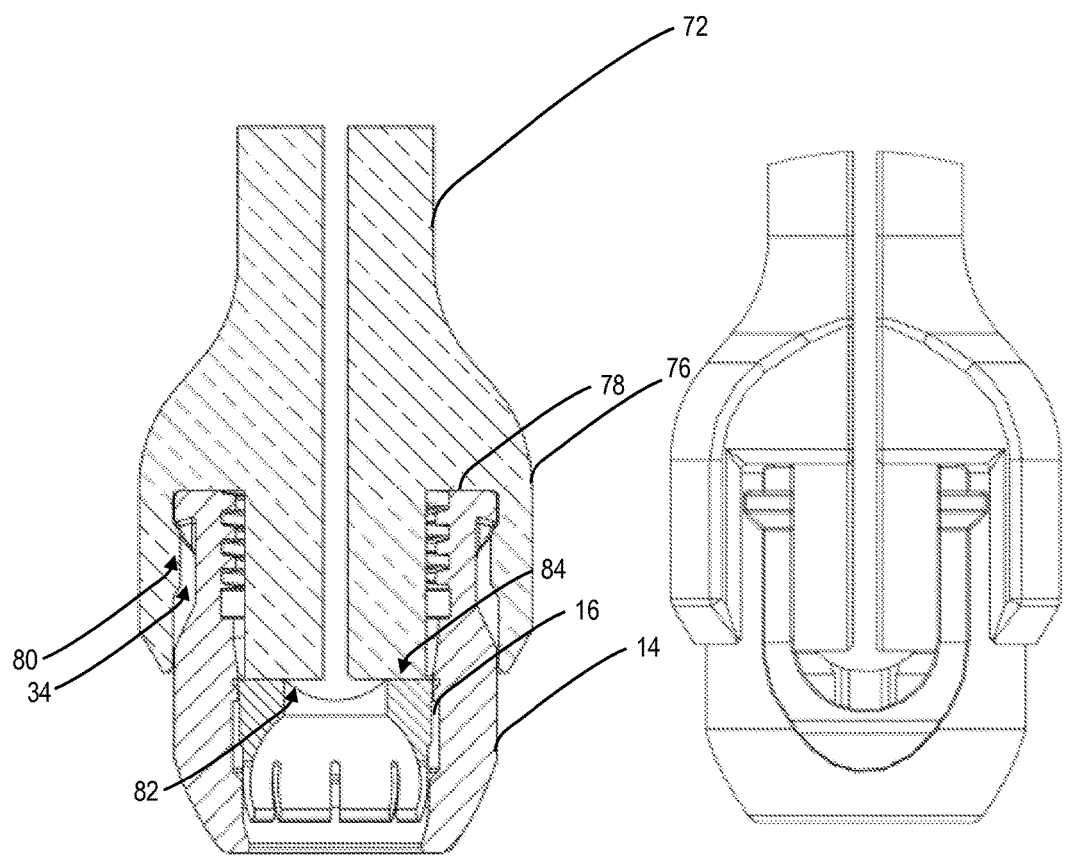
FIG. 11 is a partial cross-sectional side view of one exemplary embodiment of the head body retention and placement instrument of the present invention, with the engaged head body and saddle assembly.

Referring now specifically to FIGS. 10 and 11, in one exemplary embodiment, the proximal end of the elongate shaft portion 72 includes a pair of elongate structures 76 that selectively engage elongate sides 78 of the head body 14. As alluded to previously, the elongate structures 76 can each include an interior protruding portion 80 that engages the corresponding recess 34 manufactured into the outside of each of the elongate sides 78 of the head body 14. Using this mechanism, the instrument can be "snapped" onto and "snapped" off of the head body 14, and thereby used to "snap" the head body 14 and saddle assembly 16 onto the head end 24 (FIGS. 2 and 7-9) of the threaded screw portion 12 (FIGS. 1, 2, and 7-9). The proximal end of the elongate shaft portion 72 includes a central boss 82 that is disposed within the interior portion of the head body 14 and abuts the flat upper surface 84 of the saddle assembly 16, thereby preventing the saddle assembly 16 from backing out of the first locking position 58 (FIGS. 8 and 9) during bone anchor assembly.

Figure 12:
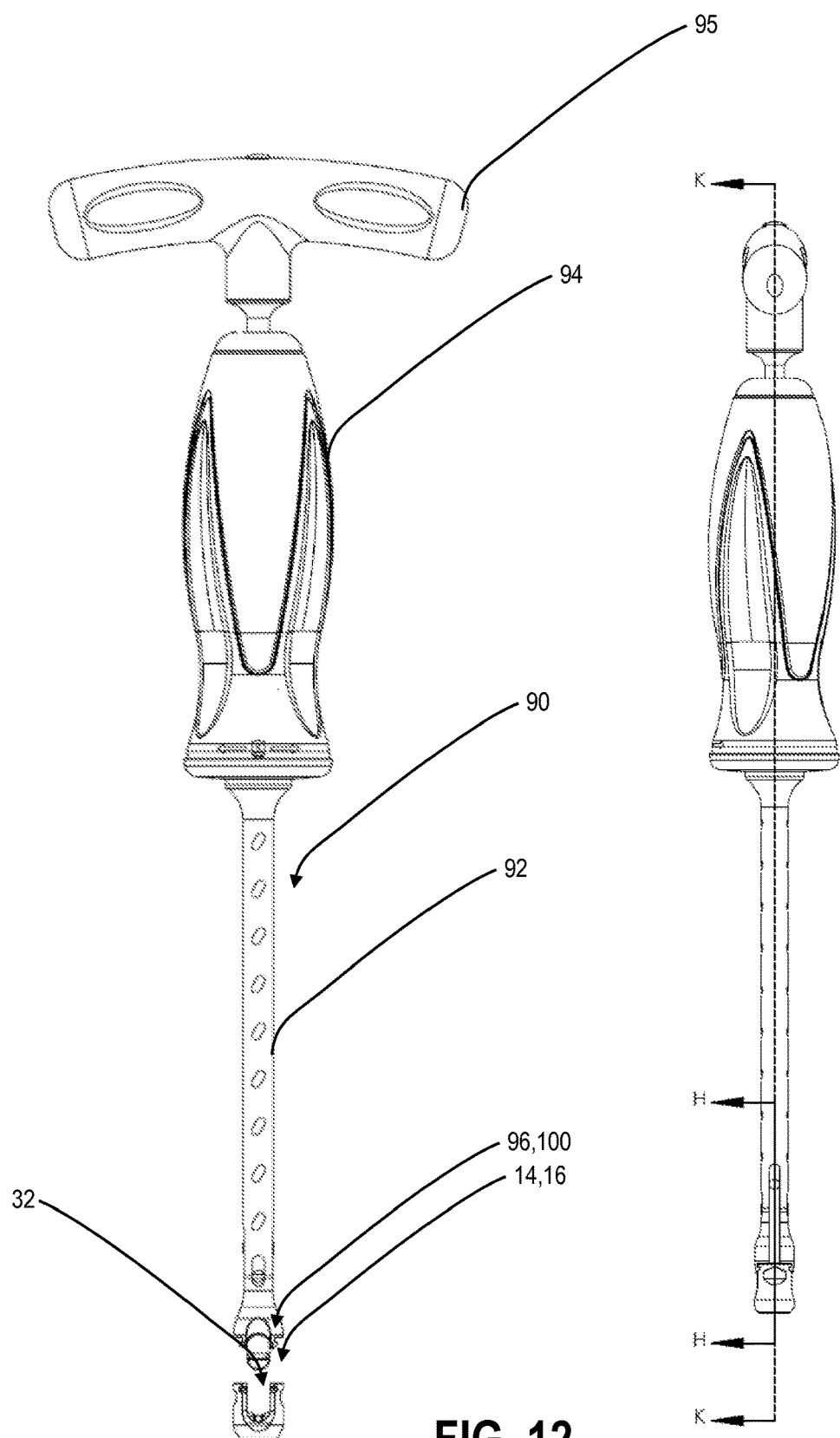
FIG. 12 is a side view of another exemplary embodiment of the head body retention and placement instrument of the present invention, with an engaged head body and saddle assembly.

Referring now specifically to FIG. 12, in another exemplary embodiment, the head body retention and placement instrument 80 includes an elongate shaft portion 82. The head body 14 and saddle assembly 16 are selectively coupled to a proximal end of the elongate shaft portion 82. A distal end of the elongate shaft portion 82 includes a handle portion 84 and actuation portion 85, by which the instrument is manipulated and actuated.

Figure 13:
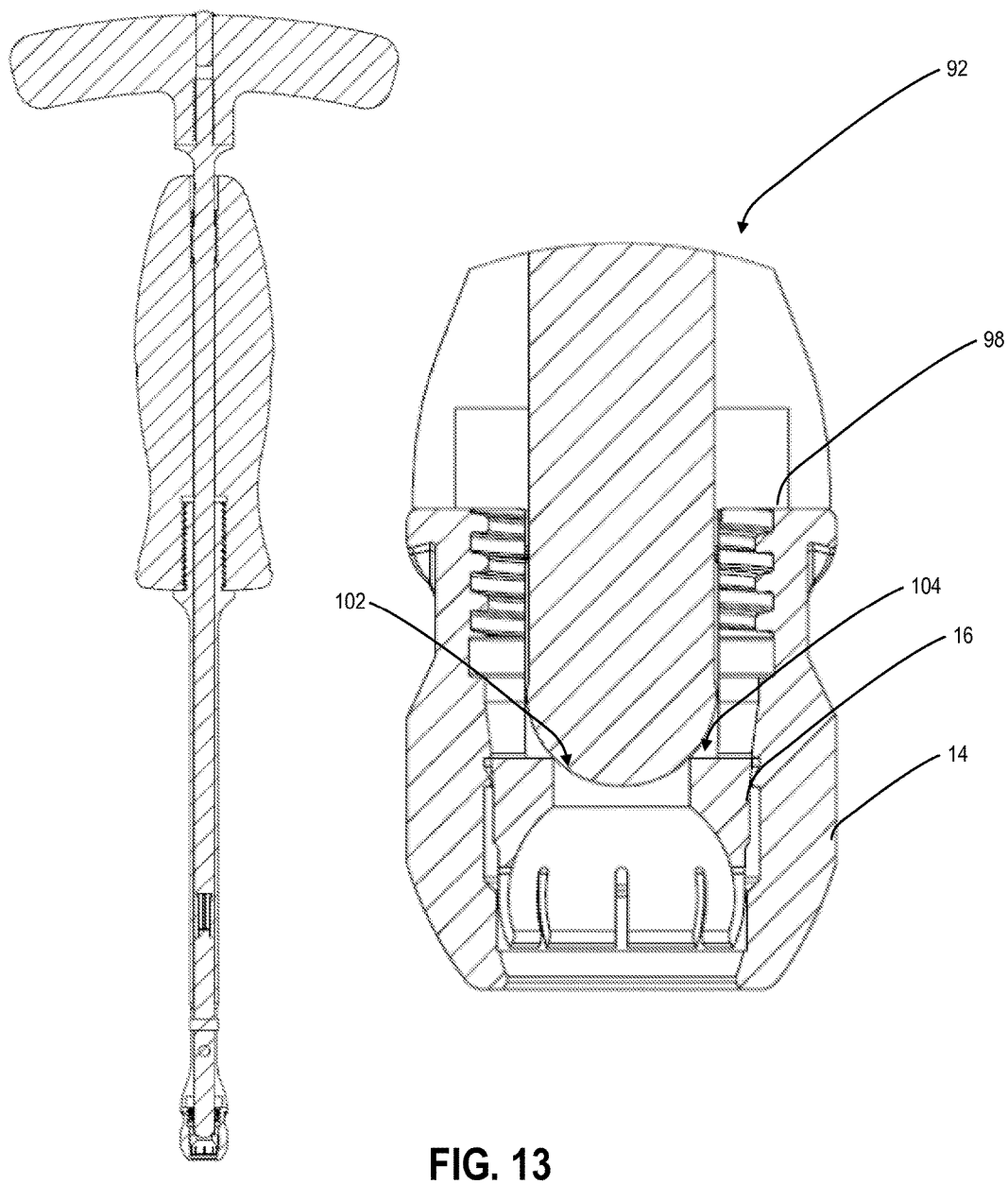
FIG. 13 is a cross-sectional side view of one exemplary embodiment of the head body retention and placement instrument of the present invention, with the engaged head body and saddle assembly.

Referring now specifically to FIGS. 12 and 13, in another exemplary embodiment, the proximal end of the elongate shaft portion 92 includes a pair of protruding structures 96 that selectively engage elongate sides 98 of the head body 14. As alluded to previously, the protruding structures 96 can each include an exterior protruding portion 100 that engages the corresponding recess 32 manufactured into the inside of each of the elongate sides 98 of the head body 14. Using this mechanism, the instrument can be "snapped" onto and "snapped" off of the head body 14, and thereby used to "snap" the head body 14 and saddle assembly 16 onto the head end 24 (FIGS. 2 and 7-9) of the threaded screw portion 12 (FIGS. 1, 2, and 7-9). The proximal end of the elongate shaft portion 92 includes a central boss 102 that is disposed within the interior portion of the head body 14 and abuts the flat or recessed upper surface 104 of the saddle assembly 16, thereby preventing the saddle assembly 16 from backing out of the first locking position 58 (FIGS. 8 and 9) during bone anchor assembly. This introducer 90 has three positions controlled by a thread and rotating the top handle 95. The first position is with the thread all the way retracted which causes a pin to splay open the bottom tine portions to accept a head body 14. The second position is when the central pushing shaft 102 just comes to bear on the saddle 16 when the saddle 16 is at the first position. The third and final position is when the handle 95 is fully rotated to urge the saddle 16 into the second position, being fully coupled axially engaged but pivotally rotatable on the screw's spherical portion 24.

Although the present invention is illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the present invention, are contemplated thereby, and are intended to be covered by the following non-limiting claims.

What is claimed is:
1. A polyaxial bone anchor assembly, comprising:
a threaded screw portion comprising a head end;
a head body disposed concentrically about the head end of the threaded screw portion, wherein the head body defines an internal bore comprising a first shoulder with an internal diameter D2 defining a first recess below the first shoulder and a second shoulder with an internal diameter D3 defining a second recess below the second shoulder; and a saddle assembly disposed within the internal bore defined by the head body and engaging the head end of the threaded screw portion, wherein the saddle assembly has a terminating end with an external diameter D1 that is larger than D2 and D3;

wherein, when the saddle assembly is translated within the internal bore defined by the head body into the first recess below the first shoulder, the head body is coupled to the threaded screw portion such that disengagement of the head body from the threaded screw portion is prevented, and, when the saddle assembly is translated within the internal bore defined by the head body into the second recess below the second shoulder, the head body is coupled to the threaded screw portion such that relative movement between the head body and the threaded screw portion is prevented.

2. The polyaxial bone anchor assembly of claim 1, wherein the saddle assembly is translated within the head body via a rod disposed adjacent to the saddle assembly, wherein the rod is disposed partially within the head body through at least one recess manufactured into a side of the head body.

3. The polyaxial bone anchor assembly of claim 2, wherein the rod engages a recess manufactured into an upper surface of the saddle assembly.

4. The polyaxial bone anchor assembly of claim 2, wherein the saddle assembly is translated within the head body via a set screw disposed adjacent to the rod opposite the saddle assembly, wherein the set screw comprises external threads that engage internal threads manufactured into an interior portion of the head body.

5. The polyaxial bone anchor assembly of claim 1, wherein the saddle assembly comprises a plurality of concentrically arranged deflectable petal structures disposed about a lower portion of the saddle assembly that engage the head end of the threaded screw portion.

6. The polyaxial bone anchor assembly of claim 1, wherein the head end of the threaded screw portion is disposed through a hole manufactured in a lower portion of the head body.

7. A polyaxial bone anchor assembly, comprising:
a threaded screw portion comprising a head end;
a head body disposed concentrically about the head end of the threaded screw portion, wherein the head body defines an internal bore comprising a first shoulder with an internal diameter D2 defining a first recess below the first shoulder and a second shoulder with an internal diameter D3 defining a second recess below the second shoulder; and a saddle assembly disposed within the internal bore defined by the head body and engaging the head end of the threaded screw portion, wherein the saddle assembly has a terminating end with an external diameter D1 that is larger than D2 and D3;

wherein, in a first locked position, when the saddle assembly is translated within the internal bore defined by the head body into the first recess below the first shoulder, the head body is coupled to the threaded screw portion such that disengagement of the head body from the threaded screw portion is resisted but allowed; and wherein, in a second locked position, when the saddle assembly is translated within the internal bore defined by the head body into the second recess below the second shoulder, the head body is coupled to the threaded screw portion such that relative movement between the head body and the threaded screw portion is prevented.

8. The polyaxial bone anchor assembly of claim 7, wherein the saddle assembly is press fit into the first locked position within the head body prior to the saddle assembly engaging the head end of the threaded screw portion.

9. The polyaxial bone anchor assembly of claim 7, wherein the saddle assembly is translated into the second locked position within the head body via a rod disposed adjacent to the saddle assembly, wherein the rod is disposed partially within the head body through at least one recess manufactured into a side of the head body.

10. The polyaxial bone anchor assembly of claim 9, wherein the rod engages a recess manufactured into an upper surface of the saddle assembly.

11. The polyaxial bone anchor assembly of claim 9, wherein the saddle assembly is translated into the second locked position within the head body via a set screw disposed adjacent to the rod opposite the saddle assembly, wherein the set screw comprises external threads that engage internal threads manufactured into an interior portion of the head body.

12. The polyaxial bone anchor assembly of claim 7, wherein the saddle assembly comprises a plurality of concentrically arranged deflectable petal structures disposed about a lower portion of the saddle assembly that selectively engage the head end of the threaded screw portion.

13. The polyaxial bone anchor assembly of claim 7, wherein the head end of the threaded screw portion is disposed through a hole manufactured in a lower portion of the head body subsequent to the placement of the threaded screw portion in bone.

* * * * *